United States Patent
De Bono (10) Patent No.: US 10,529,253 B2
(45) Date of Patent: Jan. 7, 2020

(54) METHOD FOR ORGANIZING INFORMATION AND GENERATING IMAGES OF BIOLOGICAL STRUCTURES AS WELL AS RELATED RESOURCES AND THE IMAGES AND MATERIALS SO GENERATED

(71) Applicant: Bernard De Bono, Cookham (GB)

(72) Inventor: Bernard De Bono, Cookham (GB)

( * ) Notice: Subject to any disclaimer, the term of this patent is extended or adjusted under 35 U.S.C. 154(b) by 465 days.

(21) Appl. No.: 15/251,139

(22) Filed: Aug. 30, 2016

(65) Prior Publication Data
US 2018/0061278 A1  Mar. 1, 2018

(51) Int. Cl.
| | |
|---|---|
| *G09B 23/30* | (2006.01) |
| *G16B 5/00* | (2019.01) |
| *G16H 50/50* | (2018.01) |
| *A61B 34/10* | (2016.01) |

(52) U.S. Cl.
CPC .............. *G09B 23/30* (2013.01); *G16B 5/00* (2019.02); *A61B 2034/105* (2016.02); *G16H 50/50* (2018.01)

(58) Field of Classification Search
CPC ........... G09B 23/30; G06F 19/00; G16B 5/00; G16H 50/50; A61B 2034/105
(Continued)

(56) References Cited

U.S. PATENT DOCUMENTS

| | | | | |
|---|---|---|---|---|
| 2010/0153082 A1* | 6/2010 | Newman | ............ | G01N 33/5008 703/11 |
| 2013/0034907 A1* | 2/2013 | Collins | ................. | C12N 15/63 435/455 |
| 2014/0114987 A1* | 4/2014 | Hoeng | ..................... | G06N 5/02 707/748 |

(Continued)

OTHER PUBLICATIONS

Bernard de Bono,Pierre Grenon,Stephen John Sammut, "ApiNATOMY: A Novel Toolkit for Visualizing Multiscale Anatomy Schematics with Phenotype-Related Information", Mar. 5, 2012, Wiley Periodicals, pp. 837-848.*
(Continued)

*Primary Examiner* — Jack Yip
(74) *Attorney, Agent, or Firm* — Woodard, Emhardt, Henry, Reeves & Wagner, LLP; William McKenna (57) ABSTRACT

The invention is a method for organizing biomedical resource information and generating images and text by depicting, describing and relating biological structures, biological measurements and biological processes through the association of digital graphs and digital templates, the computer programmes and databases for performing the method, and the images, text and animations so generated. The method makes use of rules to lay out circuit diagrams consisting of depictions of biological processes, measurements, and biological structures that participate in biological processes. In the circuit diagram the transition process of physical entities such as materials, or forms of energy like heat, or energy density like pressure, is drawn as a graph of lines and nodes. In the circuit diagram, the biological structures conveying or participating in the transition process are drawn as two-dimensional or three-dimensional layered units representing the structure of conveying conduits and their content. In the circuit diagram, the lines and nodes representing a transition process are overlaid onto the asymmetric units of conduits and their content. The method is applied to generate consistent displays of visual depictions of biological structures, biological measurements and biological processes at all scales of size and complexity. A result of the performance of the invention is the production of meaningful and usable depictions of complex biological processes, biological measurements, biological structures and their associated biomedical resources.

19 Claims, 9 Drawing Sheets

(58) Field of Classification Search
USPC .......................................................... 434/267
See application file for complete search history.

(56) References Cited

U.S. PATENT DOCUMENTS

2015/0220838 A1* 8/2015 Martin ..................... G06N 5/04
706/12
2015/0269870 A1* 9/2015 McGill .................... G09B 5/02
434/295

OTHER PUBLICATIONS

De Bono B., Grenon P., Helvensteijn M., Kok J., Kokash N., "ApiNATOMY: Towards Multiscale Views of Human Anatomy", Advances in Intelligent Data Analysis XIII. IDA Oct. 2014, 2014, Lecture Notes in Computer Science, vol. 8819; p. 1-13 (Year: 2014).*

P. J. Hunter and B. de Bono, "Biophysical constraints on the evolution of tissue structure and function", 2014, J Physiol 592.11 (2014) pp. 2389-2401 (Year: 2014).*

De Bono et al. "ApiNATOMY: A novel toolkit for visualizing multiscale anatomy schematics with phenotype-related information," Hum. Mutat., vol. 33, No. 5, pp. 837-848, May 2012.

De Bono et al. "Functional tissue units and their primary tissue motifs in multi-scale physiology," J. Biomed. Semant., vol. 4, No. 1, p. 22, Oct. 2013.

De Bono et al. "The Open Physiology workflow: modeling processes over physiology circuitboards of interoperable tissue units," Front. Physiol., vol. 6, p. 24, 2015.

* cited by examiner

Connectivity attachment operations for open borders of asymmetric units a) Tube attached end-to-end to Tube gives rise to Tube plus — gives rise to:

b) Bag attached end-to-end to Tube gives rise to Bag plus — gives rise to:

c) Bag attached end-to-end to Bag gives rise to Cyst plus — gives rise to:

METHOD FOR ORGANIZING INFORMATION AND GENERATING IMAGES OF BIOLOGICAL STRUCTURES AS WELL AS RELATED RESOURCES AND THE IMAGES AND MATERIALS SO GENERATED

FIELD OF INVENTION

The invention relates to a method, system and products to manage, search and display knowledge about multiscale anatomical, cellular and molecular structure as well as related biomedical resource information.

BACKGROUND OF THE INVENTION

Practice, research and training in biomedicine generate considerable amounts of electronic data and computational models, which are known in the art as biomedical resources. A significant proportion of such resources carry information that cross-references biological structures, such as anatomical, cellular and molecular structures. Examples of biomedical resources include a surgical report detailing a surgical procedure involving the stomach, a microscopy image of a liver cell, and a biochemical model of a glucose metabolic pathway.

The knowledge domains of anatomy, physiology and functional anatomy are branches of the domain of biology knowledge. The knowledge domain of anatomy is concerned with the study of the material and structural features of biological structures and their parts, ranging from whole organisms to the molecular constituents of their component cells. The knowledge domain of physiology deals with physical interactions between biological structures. The knowledge domain of functional anatomy provides an account of how the structural layout of biological structures is organized to fulfill physiological interactions.

It is desirable that functional anatomy knowledge about biological structures informs the schematic depictions of said structures so that the resulting visual composites of reference illustrations and related biomedical resource information may serve as visual aids to education, research and clinical practice by the biomedical community.

The management of biomedical resources, such as the actions of indexing, classification, comparison and searching of data and models carried out by computers operating through appropriate programming, is the subject of extensive efforts by members of the biomedical community. In particular, effective management of resources from different scales requires effective visualisation tools that display information about these resources in a meaningful way. An effective approach to achieving visualisation is to display resource information in the context of biological structures related to these resources.

The consistent visual depiction of biological structures for functional anatomy requires the complex arrangement of anatomical parts to be laid out within the constraints of scale imposed by the medium in which they are drawn. Automating the consistent visual depiction of biological structures across multiple scales is technically difficult to achieve, such that biologists and biomedical professionals have had to rely on manual methods to create complex visual representations. For instance, the generation of small-scale cellular depictions of complex structures, such as cells in bones or kidneys, is constrained by the limitation imposed by the size of the media used for those depictions. This means that descriptions of larger scale features of large structures, such as whole bones and whole kidneys, and the functional relationships between large structures and their parts, such as cells or molecules within these cells, must be omitted or may only be achieved through cumbersome manual systems of annotation and linking between separate illustrations. A well-designed method to consistently generate visually meaningful schematics of anatomically- or physiologically-related biological structures is therefore required to automatically organize and describe biomedical resources relevant to biological structures and their functional anatomy.

SUMMARY OF THE INVENTION

The present invention is a method concerned with the generation of consistent schematic depictions of the functional anatomy of biological structures, independently of scale, to provide a diagrammatic context to biological processes, biological measurements and biomedical resources that are related to such biological structures. Specifically, the use of the invention displays information about biological processes, biological measurements and biomedical resources in context by overlaying graphical representations of such information onto a schematic diagram of the biological structure or structures with which this information is associated.

According to the invention, the consistency of schematizing functional knowledge about biological structures relies on a method that identifies, independently of scale, recurrent topological features of biological structures that are relevant for these objects to fulfill their physiological role. In particular, this invention provides a consistent method to depict those functional features in biological structures that contribute to the physical interactions between anatomical parts. An example of a set biological structures interacting across scales from the domain of urinary physiology consists of a membrane channel molecule, an epithelial cell, a nephron and a urinary bladder. While these biological structures are of considerably different absolute size, their functional role imposes a consistency in their topological features that are necessary for these objects to fulfill their physiological function. In the case of this example, all four biological structures in the set are said to have rotational symmetry along their long axis such that the three-dimensional characteristics of these biological structures can be summarized using a two-dimensional graphical template that can undergo rotation around the long axis to recapitulate the three-dimensional structure. According to the invention, this two-dimensional graphical template is referred to as an asymmetric unit for a biological structure. In the case of this urinary example, the key topological features that are relevant for the four biological structures to fulfill their physiological role as conduits are identified as the presence of an outer layer of solid material wall and an inner layer of non-solid material inside the lumen of the structure. According to this invention, for example and not by way of limitation, all four biological structures in the example set can be minimally described in terms of four corresponding asymmetric units such that each asymmetric unit has:

a border that is parallel to and represents the axis of rotation;
  an inner layer, representing non-solid material inside the lumen of the biological structure, that is drawn entirely parallel and closest to the axis of rotation;
  an outer layer, representing solid material of the wall of the biological structure, that is primarily drawn parallel to, and farthest from, the axis of rotation;

terminal borders that are orthogonal to the axis of rotation representing the ports of attachment connectivity of the conduit with other conduits.

According to the invention, an asymmetric unit can be visualized as two-dimensional diagram and/or as three-dimensional projection of the complete or partial rotation of the two-dimensional diagram over the axis of rotation.

According to the invention, an asymmetric unit or its three-dimensional projection can be classified to a topological class that describes the functional role in physiology of the biological structure that the asymmetric unit represents. In the case of the above example from urinary physiology, for example and not by way of limitation:

- the membrane channel and the urinary bladder both belong to the topological class tube, defined as a conduit that has open terminal borders on both ends;
- the nephron belongs to the topological class bag, defined as a conduit that has closed terminal border and an open terminal border;
- the epithelial cell belongs to the topological call cyst, defined as a conduit that has closed terminal borders on both ends.

Graphically, the closing of terminal borders may be stylized by bending a portion of the outer layers so that this portion runs parallel to the terminal border on the side of the asymmetric unit where the terminal border is closed.

In functional anatomy, the complexity of tissue architecture can be organized by representing tissue structure at a particular scale in terms of a physical assembly of biological structures at a lower scale. For example, the wall of the small intestine conduit consists of assemblies of conduits from a smaller scale, such as blood vessels, lymphatic vessels and neurons. According to the invention, the representation of physical assemblies of biological structures from the same scale can take the form of a coalescence of asymmetric units. In a coalescence, asymmetric units are drawn to show a single shared representation of their outermost layer to denote the coalescence of the outermost layer of the biological structures that the said asymmetric units represent. For example and not by way of limitation, two conduits, one conduit represented by an asymmetric unit with an inner layer of urinary fluid, a middle layer of epithelium and an outer layer of basement membrane and the other conduit represented by an asymmetric unit with an inner layer of blood, a middle layer of endothelium and an outer layer of basement membrane, can be represented to coalesce by sharing the representation of their outermost basement membrane layers.

In anatomy, a biological structure can be said to be a constituent or a component part of another biological structure. According to the invention, the representation of parthood between biological structures can take the form of nesting of asymmetric units such that the asymmetric unit of the contained biological structure is drawn inside the asymmetric unit of the containing biological structure. The contained asymmetric unit is therefore placed within a containing asymmetric unit such that the biological structure represented by the contained asymmetric unit is asserted to be a part or a component or a region or a constituent of the biological structure represented by the containing asymmetric unit.

In the domain of physiology, the depiction of physical interaction between biological structures can take the form of a process graph that illustrates the physical transformation from one form of energy or energy density into another form of energy or energy density within a biological structure or the transfer between biological structures of energy, energy density or mass of material. According to the invention, nodes and edges from a process graph can be laid out over asymmetric units that represent biological structures that participate in or contribute to the process. In such a case, the biological structure represented by the asymmetric unit is said convey the process represented by the process graph nodes and edges placed within the asymmetric unit schematic.

The application and products of the present invention may be used to study and organize knowledge of biological structures, biological processes in which these structures participate, and information about biomedical resources related to said structures and processes. Such information is of significant interest, for example, in medical practice and pharmaceutical research, particularly to organize electronic health record data and experimental data relevant to the mechanism of a disease or the activity of a drug. The application and products deriving from the application of the method of this invention, therefore, provide great power and flexibility in the study and organization of biomedical knowledge.

Further features and advantages of the present invention, as well as the structure and operation of various embodiments of the present invention, are described in detail below with reference to the accompanying drawings.

DESCRIPTION OF PREFERRED EMBODIMENTS OF THE INVENTION

Definition of Terms

Biomedical resource—a source of information that is typified by an electronic dataset, whether text or image or computational model, and bearing biomedical significance.

Biological structure—a material biological object such as an assembly or the whole or part of an organism, including viruses, an internal organ of an animal, a single cell of a plant, a molecular complex or a single ion.

Biological process—an interaction within or between biological structures over time, such that the interaction entails:
  the physical transformation within a biological structure from one form of energy or energy density into another form of energy or energy density such as the transformation of chemical energy into heat; or
  the transfer between biological structures of energy, energy density or mass such as the mass movement of material aggregates of molecules and ions from kidney to urinary bladder.

Biomedical Data—information generated about biological structures or biological processes through the recording of relevant measurements or through calculations.

Graph—a representation of a set of objects where some pairs of objects are connected by links. The interconnected objects are represented by mathematical abstractions called vertices also called nodes or points and the links that connect some pairs of vertices are called edges also called arcs or lines.

Process graph—a graph consisting of nodes and edges depicting a biological process such as the flow of blood or the flow of electrical current or the transfer of stress or the conversion from one molecular form to another.

Conveying conduit—a biological structure is said to convey a process if the said biological structure is a required conduit for the said process to occur, for example, an enzyme is required for a molecular conversion within a biological structure such as a cell, a membrane channel is required for an electrical current to transfer from the inside of a cell to the outside of a cell, a tendon is required for the transfer of stress energy from a muscle to a bone, or a trachea is required for the transfer of air between the outside of the body and the lungs.

Asymmetric unit—a two-dimensional diagram that represents the structural characteristics of a biological structure such that the two-dimensional diagram summarizes the topological ordering or contiguity of the layers of the biological structure and/or terminal borders of the biological structure and/or the axis of rotation of the biological structure.

Coalescence—the physical fusion of the outermost layers of biological structures that are known to have a layered three-dimensional structure.

Parthood—the relation between two biological structures such that a biological structure is said to be a component, a region or a constituent, or a part of another biological structure.

Figure 9:
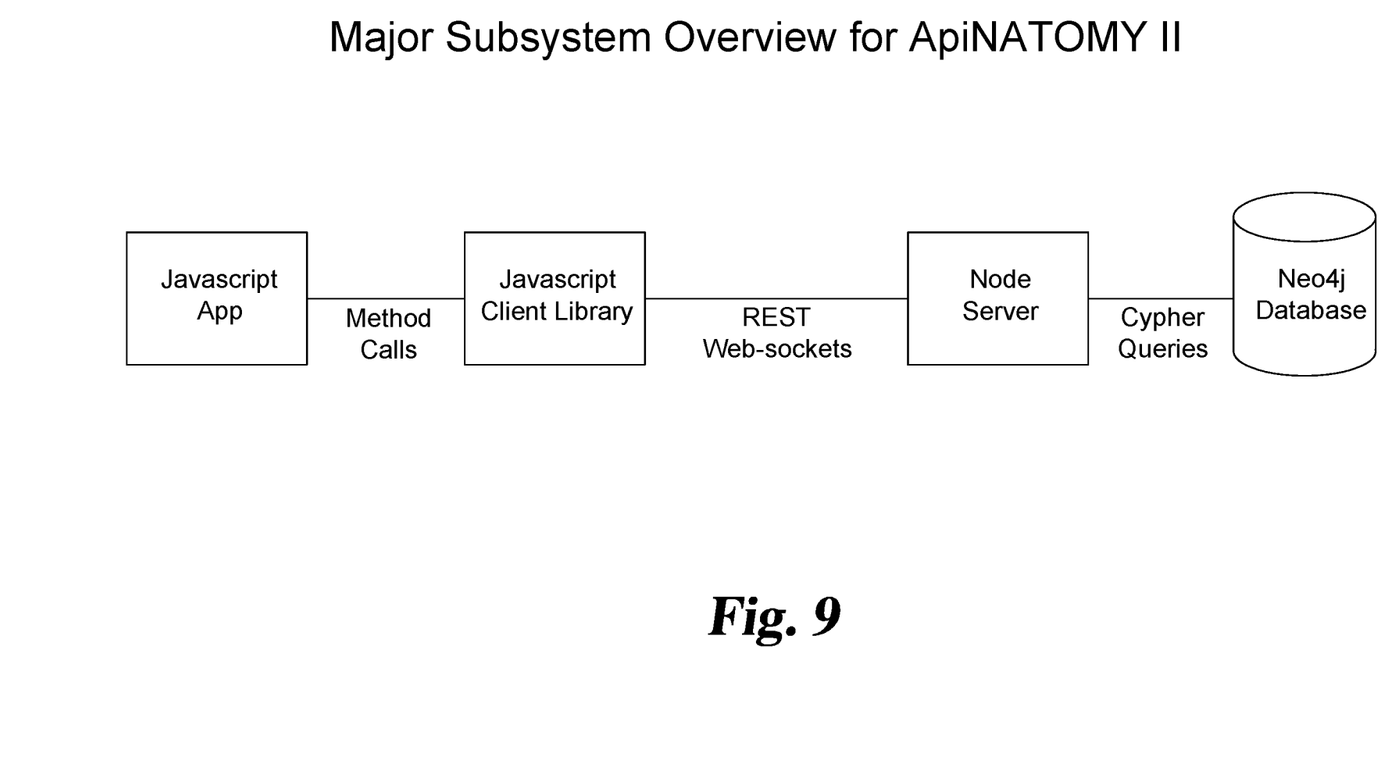
FIG. 9 is a schematic diagram showing a major subsystem overview of ApiNATOMY II.

The inventor has developed ApiNATOMY II method and its related software tools to study and organize knowledge of biological structures, biological processes in which these structures participate, and information about biomedical resources related to said structures and processes (References about work on prior versions of this software, referred to as ApiNATOMY I, are: de Bono, 2012; de Bono, 2013; de Bono, 2015). ApiNATOMY II supports the consistent schematization of biological structure visualization and provides an understanding of functional interactions between biological structures. ApiNATOMY II is stored in memory within a host computer system including one more computers responsible for maintaining ApiNATOMY II. Knowledge about biological structures, biological processes in which these structures participate, and information about the relationship between relevant biomedical resources and the said structures and processes, is authored and/or viewed by the user of ApiNATOMY II. Images and/or text defining biological structures and/or biological processes and/or related biomedical resources in ApiNATOMY II can be provided to end-users through computer connections to the host computer system allowing end-users to display consistent schematics on the monitor display screens of their computers. (See FIG. 9 for a diagram showing the major components of the ApiNATOMY II system). In this way, knowledge and information about biological structures and/or biological processes and/or related biomedical resources can be electronically managed, located and/or visualized.

Details concerning the application of the method of this invention as applied in ApiNATOMY II will be exemplified by following the operational steps in authoring the functional anatomy schematics of the tissue architecture in the kidney relevant to the flow transport of sodium in urine, the flow transport of sodium in blood, and the flow transport of sodium between urine and blood. Although examples and embodiments are described here within the context of kidney tissue architecture, and the relationship of this architecture to processes of flow transport of sodium in urine, the flow transport of sodium in blood, and the flow transport of sodium between urine and blood, embodiments are not limited thereto.

Figure 8:
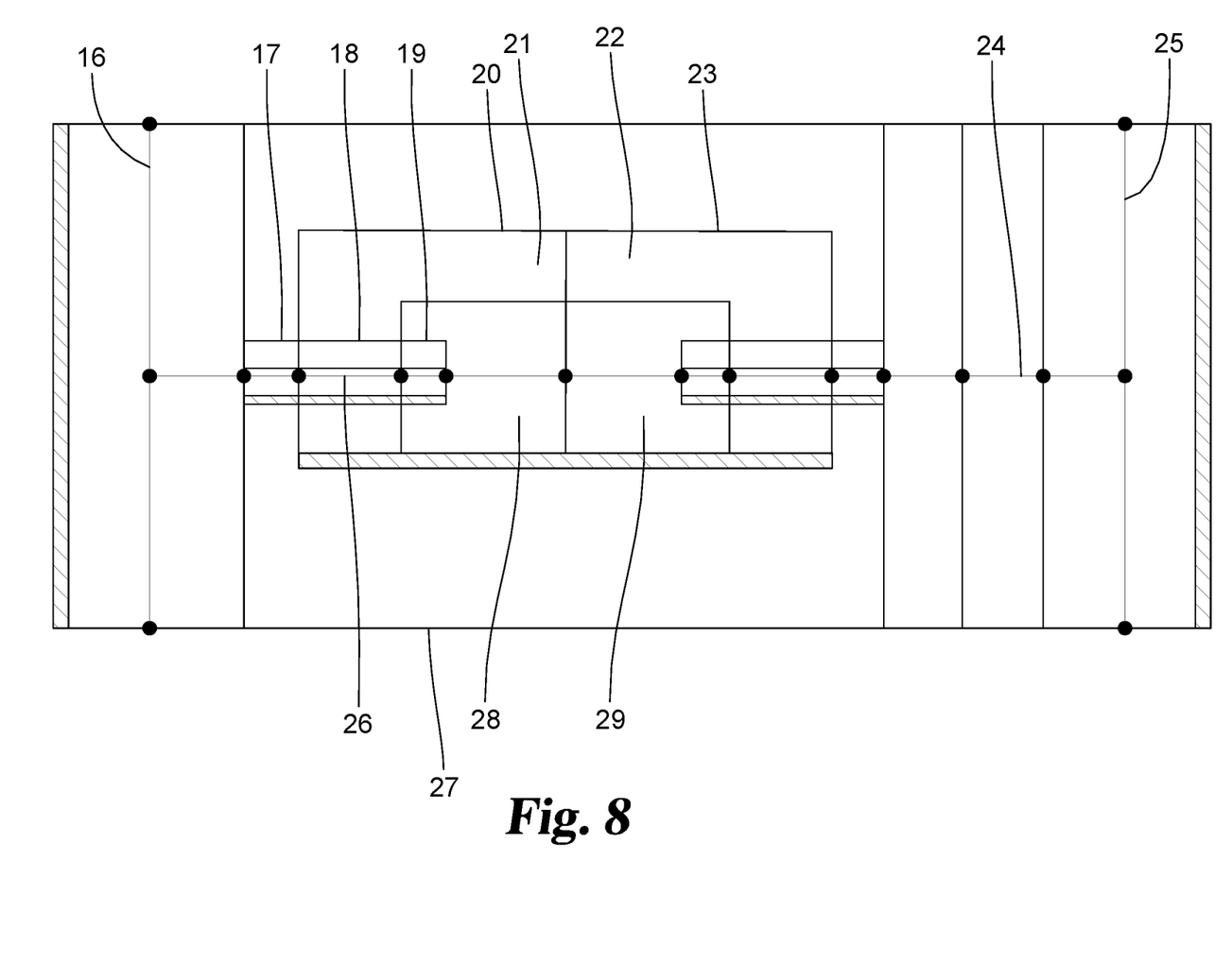
FIG. 8 provides a circuit diagram of complex interactions between biological structures from different scales such that the organization, orientation and nesting of asymmetric units provides both anatomical context and functional meaning to a process graph laid out over the structural schematics.

According to certain embodiments of the invention, an operator can make use of ApiNATOMY II to consistently describe the tissue architecture of the functional anatomy of the kidney as a set of schematics of asymmetric units. The operator may then use this set of schematics of asymmetric units to organize a graph representing the process of flow transport of sodium in urine, the flow transport of sodium in blood, and the flow transport of sodium between urine and blood such that the final result for this circuit diagram example is shown in FIG. 8.

Figure 1:
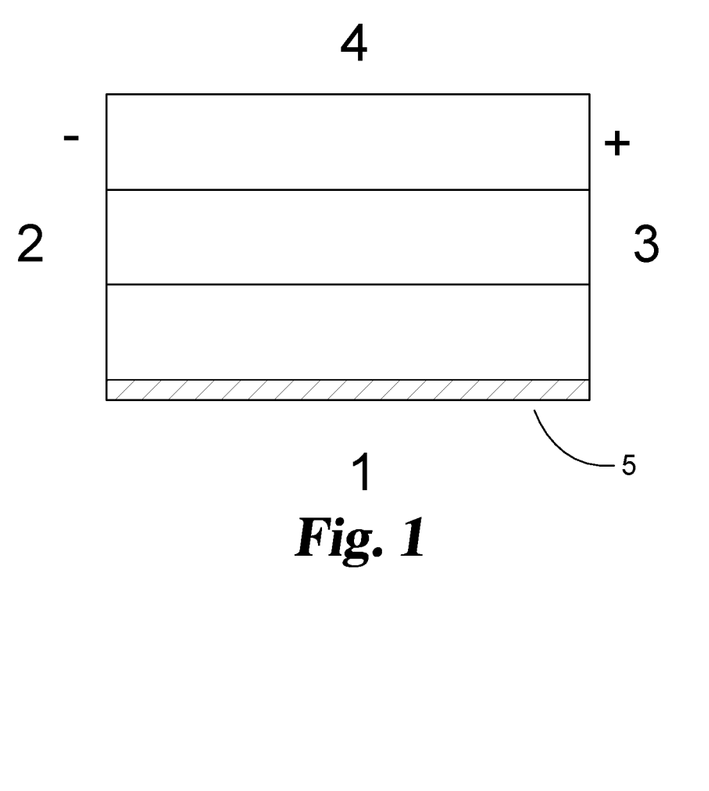
FIG. 1 shows a two-dimensional asymmetric unit, consisting in this example of three layers, together with the rotational axis for the asymmetric unit depicted as a diagonally hatched line. To differentiate the two terminal borders on the right and left of the schematic, the asymmetric unit schematic may include distinctive symbols, such as the '+' and '−' sign, to explicitly mark the polarity of the asymmetric unit.
Figure 4A:
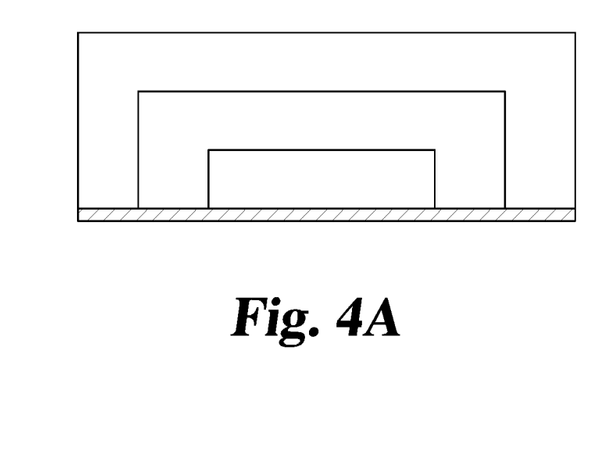
FIG. 4A shows a two-dimensional asymmetric unit of topological class cyst, consisting in this example of three layers, together with the rotational axis for the asymmetric unit depicted as a diagonally hatched line. On both sides, the asymmetric unit is stylized by bending a portion of the outer layers to run parallel to the terminal borders.
Figure 4B:
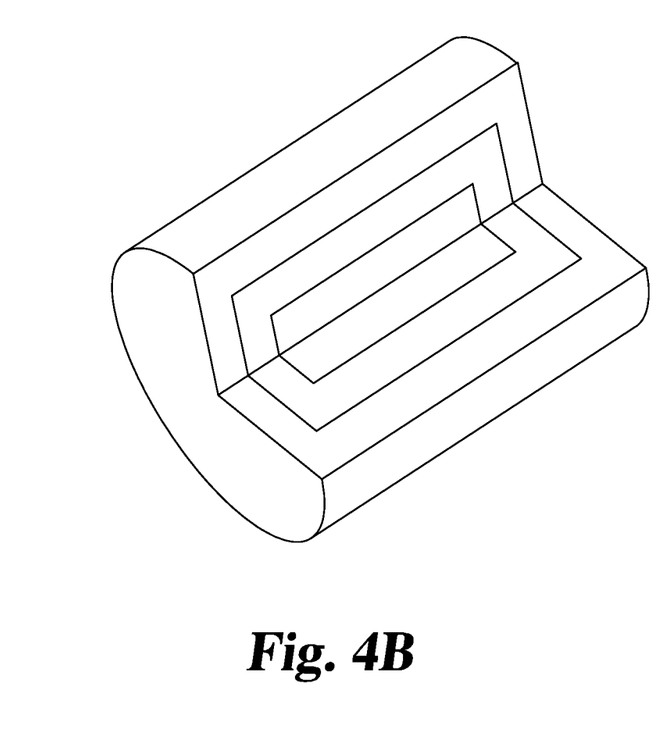
FIG. 4B shows the corresponding three-dimensional asymmetric unit of topological class cyst created through the partial rotation of the two-dimensional asymmetric unit in FIG. 4A over its rotational axis.

According to certain embodiments of the invention relevant to this kidney tissue architecture example, each asymmetric unit is drawn to have terminal borders (2 & 3 in FIG. 1) orthogonal to the axis of rotation (5 in FIG. 1), and an ordering of layers from the innermost (1 in FIG. 1) to the outermost (4 in FIG. 4) direction.

Figure 2A:
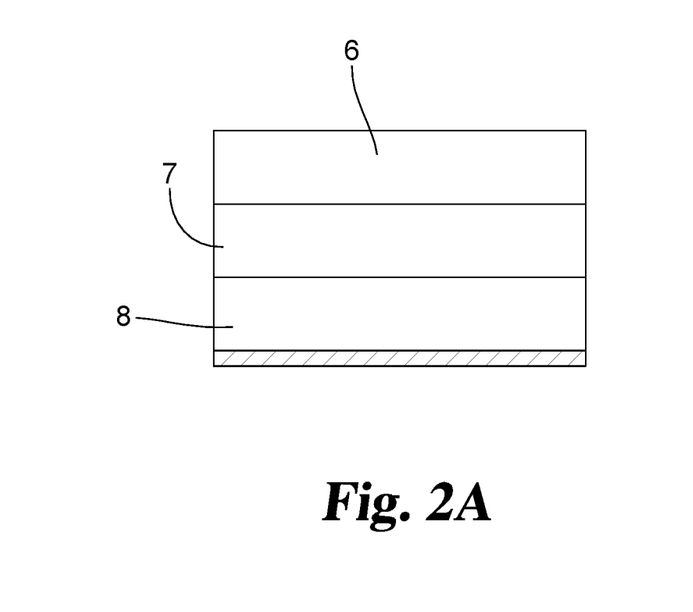
FIG. 2A shows a two-dimensional asymmetric unit of topological class tube, consisting in this example of three layers, stylized as a layered structure where the layers are entirely parallel to the axis of rotation, together with the rotational axis for the asymmetric unit depicted as a diagonally hatched line.
Figure 2B:
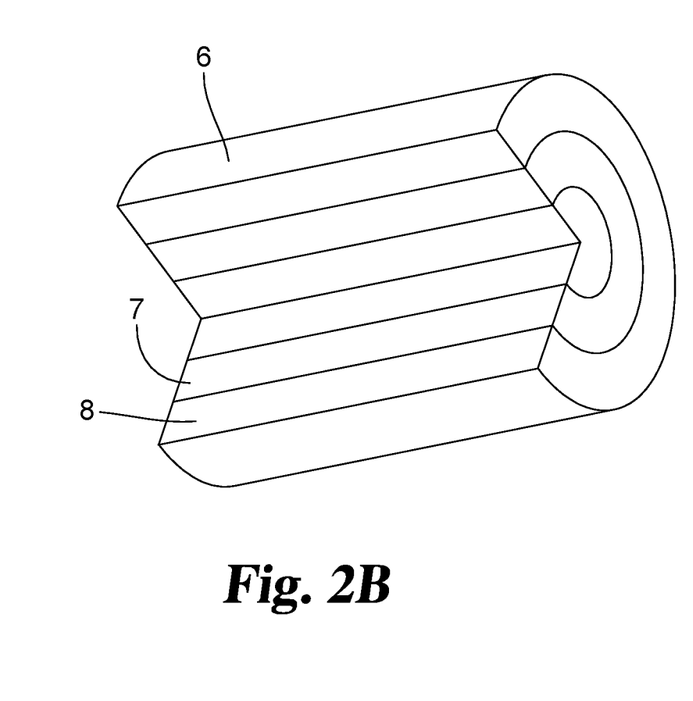
FIG. 2B shows the corresponding three-dimensional asymmetric unit of topological class tube created through the partial rotation of the two-dimensional asymmetric unit in FIG. 2A over its rotational axis.
Figure 5A:
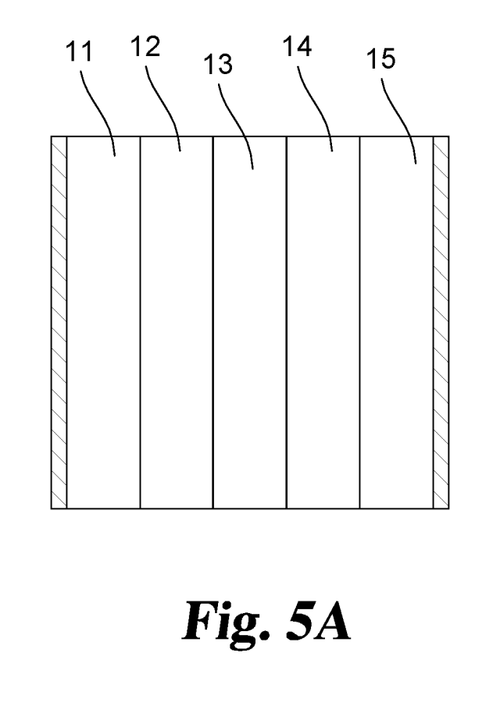
FIG. 5A shows the graphical depiction of a pair of two-dimensional asymmetric units of type tube representing two corresponding biological structures that have coalesced their outermost layer. The respective rotational axes for the two asymmetric units are depicted as diagonally hatched lines to the left and to the right.

According to certain embodiments of the invention relevant to this kidney tissue architecture example, two asymmetric units of type tube, each consisting of three layers (FIG. 2A), are created in preparation for their coalescence (FIG. 5A). The two asymmetric units of type tube represent respectively:

the architecture of the wall and the content of the lumen of an epithelial tube segment from the nephron, such that the innermost layer (8 in FIG. 2A; 11 in FIG. 5A) represents the urine content of the epithelial tube segment, the middle layer (7 in FIG. 2A; 12 in FIG. 5A) represents the epithelial layer of the epithelial tube segment, and the outermost layer (6 in FIG. 2A; 13 in FIG. 5A) represents the basement membrane layer of the epithelial tube segment;

the architecture of the wall and the content of the lumen of an endothelial tube segment from a blood vessel, such that the innermost layer (8 in FIG. 2A; 15 in FIG. 5A) represents the blood content of the endothelial tube segment, the middle layer (7 in FIG. 2A; 14 in FIG. 5A) represents the endothelial layer of the endothelial tube segment, and the outermost layer (6 in FIG. 2A; 13 in FIG. 5A) represents the basement membrane layer of the endothelial tube segment.

Biomedical resources relevant to the biological structures represented by the above two asymmetric units of type tube may be linked to these units and/or their layers. For example:

the layer of blood content of the endothelial tube segment may be associated with a biomedical resource detailing the biochemical composition of blood from an electronic health record resource, such that a graphical symbol overlaid onto the blood layer in the asymmetric unit may serve to represent the measurement of the concentration of sodium in the blood recorded by the resource.

the layer of urine content of the epithelial tube segment may be associated with a biomedical resource detailing the biochemical composition of urine from an electronic health record resource, such that a graphical symbol overlaid onto the urine layer in the asymmetric unit may serve to represent the measurement of the concentration of calcium in the urine recorded by the resource;

the layer of basement membrane of both epithelial and endothelial tube segments may be associated with a biomedical resource detailing the biochemical composition of the connective material of the basement membrane from an experimental biology resource, such that a three-dimensional graphical object overlaid onto the basement membrane layer in the asymmetric unit may serve to depict the crystal structure of a collagen molecule recorded by the resource.

Figure 5B:
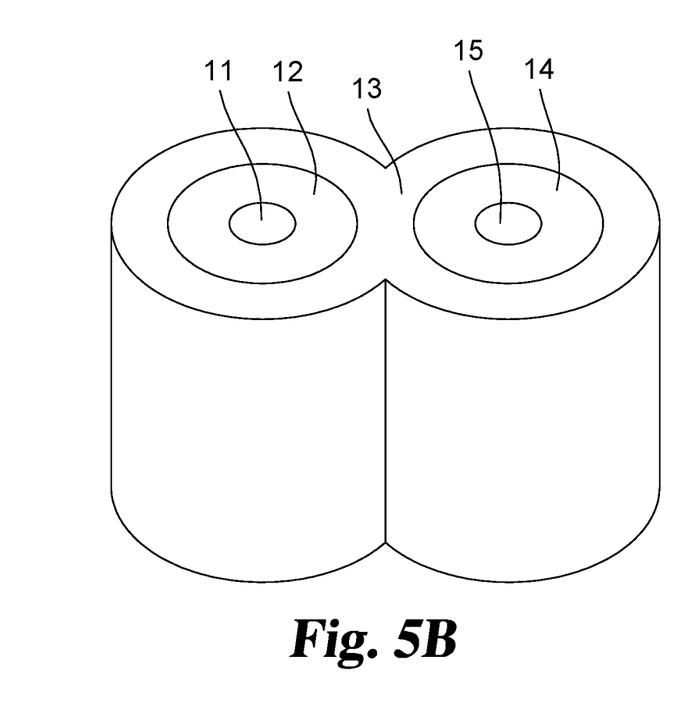
FIG. 5B shows the corresponding pair of three-dimensional coalescing asymmetric units of type tube created through the complete rotation of the two-dimensional asymmetric units in FIG. 5A over their respective rotational axes.
Figure 6:
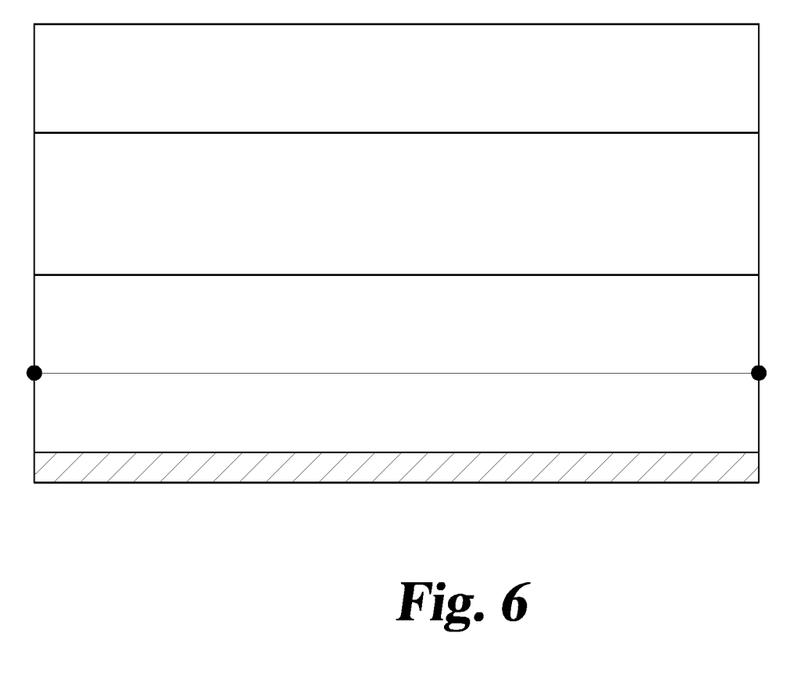
FIG. 6 shows an edge and two nodes from a process graph laid over a two-dimensional asymmetric unit of topological class tube, in this example consisting of three layers, together with the rotational axis for the asymmetric unit depicted as a diagonally hatched line. The biological structure represented by the asymmetric unit is said to be in a conveying relationship with the process represented by the two nodes and edge that are placed within the asymmetric unit.

The above two asymmetric units of type tube may brought to coalesce to created a five-layered coalescence as depicted two dimensions in FIG. 5A and correspondingly in three dimensions in FIG. 5B. The shared outermost layer is shown as 13 in FIG. 5A as well as FIG. 5B.

Figure 3A:
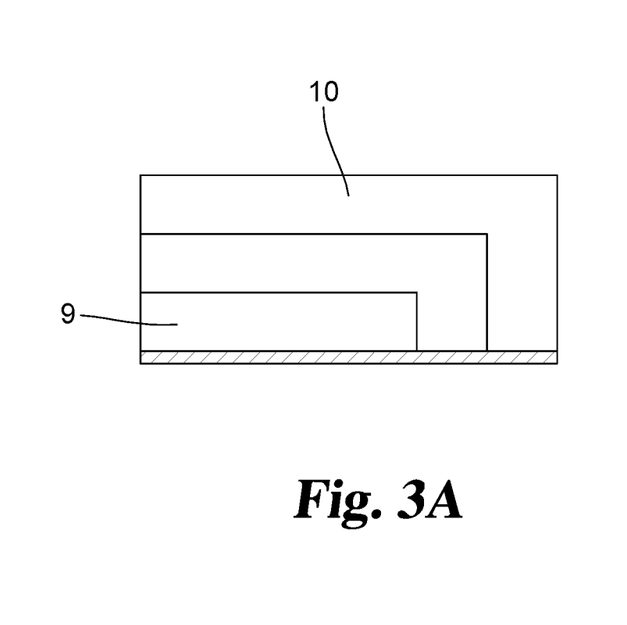
FIG. 3A shows a two-dimensional asymmetric unit of topological class bag, consisting in this example of three layers, together with the rotational axis for the asymmetric unit depicted as a diagonally hatched line. On the right, the asymmetric unit is stylized by bending a portion of the outer layers to run parallel to the terminal border on the side of the asymmetric unit where the terminal border is closed.
Figure 3B:
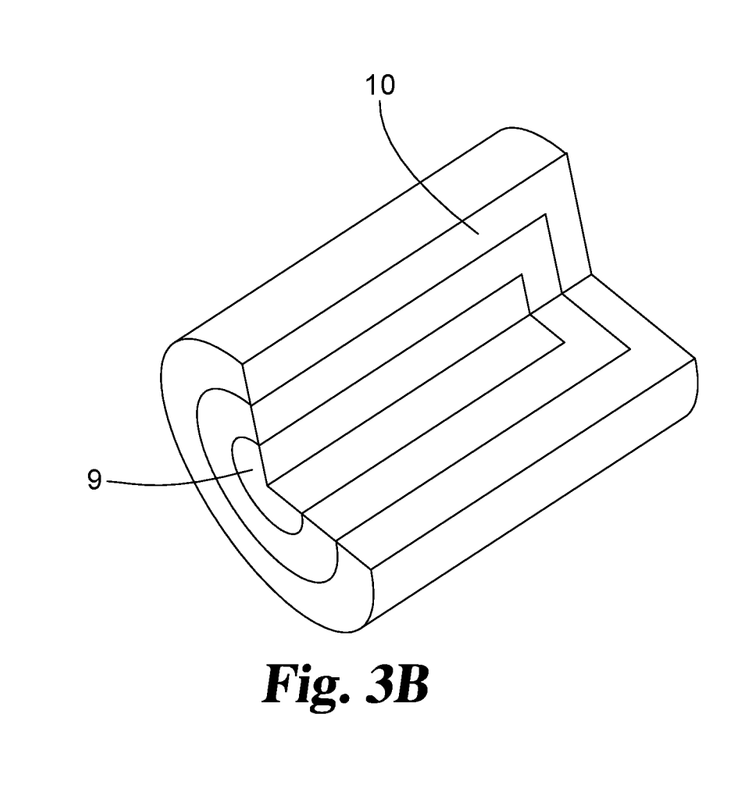
FIG. 3B shows the corresponding three-dimensional asymmetric unit of topological class bag created through the partial rotation of the two-dimensional asymmetric unit in FIG. 3A over its rotational axis.

According to certain embodiments of the invention relevant to this kidney tissue architecture example, two asymmetric units of type bag, each consisting of two layers, are created in preparation for their attachment over their open terminal border. The two asymmetric units of type bag represent respectively:

the apical region of a renal epithelial cell (20 in FIG. 8), such that the innermost layer (9 in FIG. 3A; 28 in FIG. 8) represents the cytoplasmic content in the apical region of a renal epithelial cell, and the outermost layer (10 in FIG. 3A; 21 in FIG. 8) represents the plasma membrane of the apical region of a renal epithelial cell;

the basolateral region of a renal epithelial cell (23 in FIG. 8), such that the innermost layer (9 in FIG. 3A; 29 in FIG. 8) represents the cytoplasmic content in the basolateral region of a renal epithelial cell, and the outermost layer (10 in FIG. 3A; 22 in FIG. 8) represents the plasma membrane of the basolateral region of a renal epithelial cell.

Figure 7:
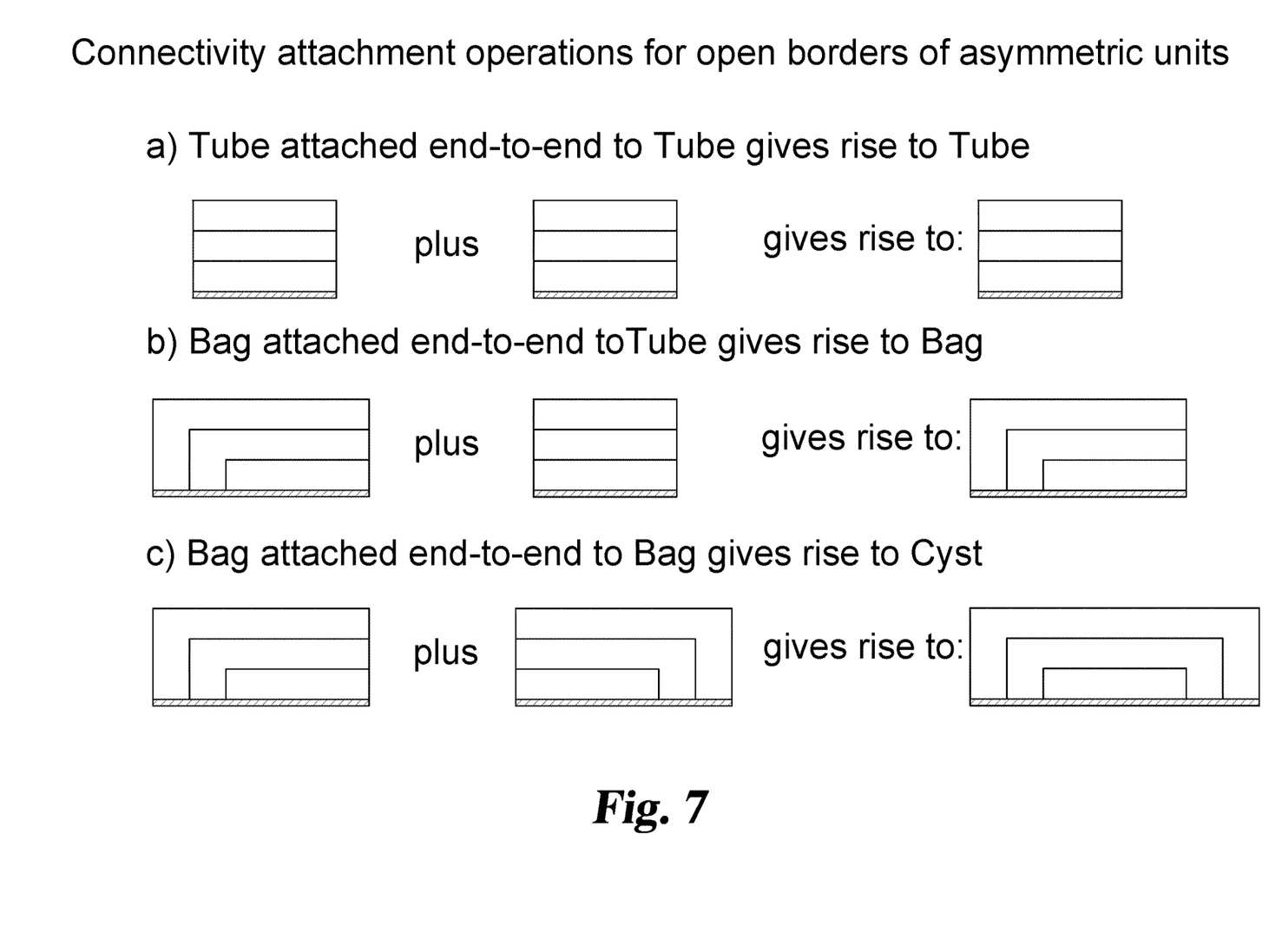
FIG. 7 describes three types of connectivity attachment operation that can be performed to the open terminal borders of asymmetric units.

The above two asymmetric units of type bag (20 & 23 in FIG. 8) may be brought to attach by their open terminal borders to create a two-layered asymmetric unit of type cyst (FIG. 4A; this attachment operation is depicted in item c of FIG. 7) that represents the renal epithelial cell in its entirety, such that the attachment of 28 & 29 in FIG. 8 graphically represents the innermost layer of this cyst and the attachment of 21 & 22 in FIG. 8 graphically represents the outermost layer of this cyst. This two-layered asymmetric unit of type cyst that represents the renal epithelial cell in its entirety may be placed in the middle layer (7 in FIG. 2A; 12 in FIG. 5A) of the asymmetric unit of type tube that represents the epithelial layer of the epithelial tube segment such that this placement asserts that the renal epithelial cell is a component part of the epithelial layer of the epithelial tube segment. Biomedical resources relevant to the biological structures represented by the above two asymmetric units of type bag may be linked to these units and/or their layers. For example:

the layer of plasma membrane of the apical region of a renal epithelial cell may be associated with a biomedical resource detailing the antibody staining patterns from a light microscopy resource;

the layer of cytoplasm of the basolateral region of a renal epithelial cell may be associated with a biomedical resource detailing organelle density from an electron microscopy resource.

According to certain embodiments of the invention relevant to this kidney tissue architecture example, three asymmetric units of type tube, each consisting of two layers, are created in preparation for their attachment over their open terminal borders. The three asymmetric unit of type tube represent respectively:

the extracellular segment of a membrane channel for sodium (17 in FIG. 8), such that the innermost layer (8 in FIG. 2A) represents the content of the lumen of the extracellular segment of the membrane channel for sodium, and the outermost layer (6 in FIG. 2A) represents the protein wall of the extracellular segment of the membrane channel for sodium;

the transmembrane segment of a membrane channel for sodium (18 in FIG. 8), such that the innermost layer (8 in FIG. 2A) represents the content of the lumen of the transmembrane segment of the membrane channel for sodium, and the outermost layer (6 in FIG. 2A) represents the protein wall of the transmembrane segment of the membrane channel for sodium;

the intracellular segment of a membrane channel for sodium (19 in FIG. 8), such that the innermost layer (8 in FIG. 2A) represents the content of the lumen of the intracellular segment of the membrane channel for sodium, and the outermost layer (6 in FIG. 2A) represents the protein wall of the intracellular segment of the membrane channel for sodium.

The above three asymmetric units of type tube may be brought to attach end-to-end over their open terminal borders to create a two-layered asymmetric unit of type tube (FIG. 2A; this attachment operation is depicted in item a of FIG. 7) that represents the membrane channel for sodium in its entirety. This two-layered asymmetric unit of type tube that represents the membrane channel for sodium in its entirety may be placed to straddle the plasma membrane layer (21 in FIG. 8) of two-layered asymmetric unit of type bag that represents the apical region of a renal epithelial cell such that:

the two-layered asymmetric unit of type tube representing the extracellular segment of a membrane channel for sodium is placed inside the middle layer (7 in FIG. 2A; 12 in FIG. 5A; 27 in FIG. 8) of the asymmetric unit of type tube representing the epithelial layer of the epithelial tube segment, but outside the two-layered asymmetric unit of type bag that represents the apical region of a renal epithelial cell (20 in FIG. 8) such that this placement asserts that the extracellular segment of a membrane channel for sodium is a component part of the epithelial layer;

the two-layered asymmetric unit of type tube representing the transmembrane segment of a membrane channel for sodium is placed inside plasma membrane layer (21 in FIG. 8) of the two-layered asymmetric unit of type bag that represents the apical region of a renal epithelial cell such that this placement asserts that the transmembrane segment of a membrane channel for sodium is a component part of the plasma membrane;

the two-layered asymmetric unit of type tube representing the intracellular segment of a membrane channel for sodium is placed inside cytoplasm layer (28 in FIG. 8) of the two-layered asymmetric unit of type bag representing the apical region of a renal epithelial cell such that this placement asserts that the intracellular segment of a membrane channel for sodium is a component part of the cytoplasm.

Biomedical resources relevant to the biological structure represented by the above two-layered asymmetric unit of type tube representing the membrane channel for sodium in its entirety may be linked to identifiers from protein databases to describe explicitly the peptide sequence or crystal structure of this membrane channel in its entirety. Biomedical resources relevant to the biological structure represented by the above two-layered asymmetric unit of type tube representing the transmembrane segment of a membrane channel for sodium may be linked to identifiers from protein databases to describe explicitly the peptide sub-sequences of the transmembrane parts of the membrane channel.

According to certain embodiments of the invention relevant to this kidney tissue architecture example, the depiction of the flow transport of sodium can take the form of a process graph that illustrates the transfer of this material. In this example, nodes and edges from a process graph representing sodium flow transport are laid out over the arrangement of kidney tissue coalescence, renal epithelial cell and membrane channel for sodium described in this example (FIG. 8) to create a circuit diagram. For example:

the pair of nodes and associated edge labeled 16 in FIG. 8 represents the flow of sodium in the urine as conveyed by the epithelial tube segment conduit;

the pair of nodes and associated edge labeled 25 in FIG. 8 represents the flow of sodium in the blood as conveyed by the endothelial tube segment conduit;

the pair of nodes and associated edge labeled 26 in FIG. 8 represents the flow of sodium in the lumen of the membrane channel for sodium as conveyed by the transmembrane segment of a membrane channel for sodium located inside plasma membrane layer of the two-layered asymmetric unit of type bag representing the apical region of a renal epithelial cell;

the pair of nodes and associated edge labeled 24 in FIG. 8 represents the flow of sodium as conveyed by the endothelial layer of endothelial tube segment conduit.

Biomedical resources relevant to the biological process of sodium flow transport represented by the above process graph may be linked to specific sets of nodes and edges, for example:

the rate of blood flow in the kidney from a vascular physiology experiment in mouse may be linked the pair of nodes and associated edge labeled 25 in FIG. 8;

the rate of sodium flux from a patch-clamp electrophysiology experiment in rat may be linked to the pair of nodes and associated edge labeled 26 in FIG. 8.

It should be understood that the examples and embodiments described herein are for illustrative purposes only and that various modifications or changes in light thereof will be suggested to persons skilled in the art and are to be included within the spirit and purview of this application.

What is claimed is:

1. A method for generating and displaying a graph of anatomically and physiologically related biological resources relevant to biological structures comprising the steps of:

establishing a plurality of asymmetric units using at least a first computer processing unit based upon a first user input, wherein each asymmetric unit represents a single type of identified biological structure and includes at least:

a defined axis of rotation around which the asymmetric unit may be rotated to create a three dimensional structure, an innermost layer which represents a first material inside the biological structure represented by the asymmetric unit having an innermost border along the axis of rotation, and an outermost layer parallel to the axis of rotation which represents a second material which forms the outer layer or wall of the biological structure represented by the asymmetric unit, and a pair of terminal borders orthogonal to the axis of rotation which each represent one of the two ports of axial attachment of the biological structure represented by the asymmetric unit;

establishing a plurality of interconnections between selected sets of the plurality of asymmetric units using the first computer processing unit based upon a second user input, wherein the plurality of interconnections includes at least one of:

an axial connection between a first and a second asymmetric unit within the plurality of asymmetric units, whereby one of the terminal borders of the first asymmetric unit is connected to one of the terminal borders of the second asymmetric unit; and a coalescent connection between a third and a fourth asymmetric unit within the plurality of asymmetric units, whereby the outermost layer of the third asymmetric unit is connected to the outermost layer of the fourth asymmetric unit;

establishing process relationships between selected sets of the plurality of asymmetric units using the first computer processing unit based upon a third user input, wherein each process relationship indicates flow of an identified material or energy within the organism between a selected portion of a fifth selected asymmetric unit and a selected portion of a sixth asymmetric unit;

generating a visual display comprising the plurality of asymmetric units and the process relationships, wherein the plurality of asymmetric units are laid out according to the plurality of interconnections and the process relationships are displayed as an overlay on top of the plurality of asymmetric units and said process relationships are represented on the visual display as a set of edges and vertices passing through at least one layer of an asymmetric unit which do not contact or cross any asymmetric units which are not involved in the indicated flow of an identified material or energy within the organism using the first computer processing unit; and displaying the visual display on an electronic monitor using the first computer processing unit.

2. The method for claim 1 wherein the visual display is two-dimensional.

3. The method of claim 1, wherein the rotational axis of each asymmetric unit is displayed as a diagonally hatched line.

4. The method for claim 1 wherein the visual display is three dimensional.

5. The method for claim 4, further comprising the step of rotating each asymmetrical unit within the plurality of asymmetrical units around its axis of rotation to generate a three-dimensional representation for inclusion in the visual display.

6. The method of claim 5, wherein said rotating of each asymmetric unit is a rotation of 360 degrees.

7. The method of claim 1, wherein the fifth and sixth asymmetric units are the same asymmetric unit.

8. The method of claim 1, wherein at least one of the plurality of asymmetric units includes one or more intermediate layers located between the innermost layer and the outermost layer.

9. The method of claim 1, wherein one of the terminal borders of at least one of the plurality of asymmetric units is a closed terminal border.

10. The method of claim 9, wherein the first and the second asymmetric units each have exactly one of their terminal borders being an open terminal border and the first and second asymmetric units are axially connected together at their open terminal borders.

11. The method of claim 9, wherein the first asymmetric unit each has exactly one of its terminal borders being a closed terminal border and the second asymmetric unit each has exactly two of its terminal borders being open terminal borders and the first and second asymmetric units are axially connected together at least one of their open terminal borders.

12. The method of claim 1, wherein both of the terminal borders of at least one of the plurality of asymmetric units are closed terminal borders.

13. The method of claim 1, wherein both of the terminal borders of at least one of the plurality of asymmetric units are open terminal borders.

14. The method of claim 13, wherein the first and the second asymmetric units each have exactly two of their terminal borders being open terminal borders and the first and second asymmetric units are axially connected together.

15. The method of claim 1, further comprising the step of overlying a graphical symbol over a selected portion of a selected asymmetric unit, wherein the graphical symbol represents biological data associated with the selected portion of the selected asymmetric unit.

16. The method of claim 1, wherein the visual display is constructed independent of scale.

17. The method of claim 1, wherein at least one terminal border of a selected asymmetric unit is labelled with a plus symbol and the other terminal border of the selected asymmetric unit is labelled with a minus symbol.

18. The method of claim 1, wherein a contained asymmetric unit is defined as residing with a containing asymmetric unit, indicating that the biological structure represented by the contained asymmetric unit is a component of the biological structure represented by the containing asymmetric unit.

19. The method of claim 1, wherein said establishing a plurality of interconnections between selected sets of the plurality of asymmetric units based upon a second user input includes each of: an axial connection between a first and a second asymmetric unit within the plurality of asymmetric units and a coalescent connection between a third and a fourth asymmetric unit within the plurality of asymmetric units.

* * * * *